United States Patent [19]

Bouchaudon et al.

[11] Patent Number: 4,868,326

[45] Date of Patent: Sep. 19, 1989

[54] PROCESS FOR THE PREPARATION OF $N^6$-BENZYLOXYCARBONYL-2,6-DIAMINOPIMELAMIC ACID IN THE L,L OR D,D OR RACEMIC FORMS

[75] Inventors: Jean Bouchaudon, Morsang sur Orge; Daniel Farge, Thiais; Claude James, Paris, all of France

[73] Assignee: Rhone-Poulenc Sante, Courbevoie, France

[21] Appl. No.: 227,780

[22] Filed: Aug. 3, 1988

[30] Foreign Application Priority Data

Aug. 7, 1987 [FR] France .................................. 87 11257

[51] Int. Cl.[4] ......................................... C07C 125/065

[52] U.S. Cl. .................................................... 560/159
[58] Field of Search ........................................ 560/159

[56] References Cited

PUBLICATIONS

Ardendt, Chem. Abstr., 82, 31497g (1975).

Primary Examiner—Michael L. Shippen
Attorney, Agent, or Firm—Stevens, Davis, Miller & Mosher

[57] ABSTRACT $N^6$-Benzyloxycarbonyl-2,6-diaminopimelamic acid in L,L or D,D or racemic form is prepared by amidation of $O^1$-p-nitrobenzyl-$N^2$-benzyloxycarbonyl-2,6-diaminopimelic acid in L,L or D,D or racemic form.

4 Claims, No Drawings

PROCESS FOR THE PREPARATION OF N⁶-BENZYLOXYCARBONYL-2,6-DIAMINOPIMELAMIC ACID IN THE L,L OR D,D OR RACEMIC FORMS

The present invention relates to the preparation of N⁶-benzyloxycarbonyl-2,6-diaminopimelamic acid of formula:

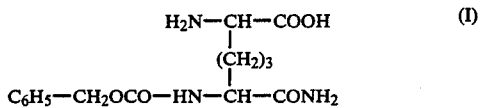

in L,L or D,D or racemic forms.

The product of formula (I) is an intermediate in the synthesis of peptides which are the subject of French Patents FR 79/16,844 (2,460,289), FR 79/16,845 (2,460,290), FR 80/11,231 (2,482,958) and FR 80/11,233 (2,482,960), and which exhibit remarkable immunostimulating properties.

According to French Patent FR 79/16,844 (2,460,289), the product of formula (I) may be obtained from 2,6-diaminopimelic acid. To this end, the dibenzyl ester of 2,6-dibenzyloxycarbonylaminopimelic acid is prepared by known methods, and is monosaponified according to the method described by A. Arendt et al., Roczniki Chemii Ann. Soc. Chim. Polonorum, 48, 1305 (1974) [Chem. Abstr., 82, 31497 g (1975)] and is then converted, by reaction with ammoniacal methanol, into a monoamide of formula:

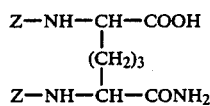

in which Z denotes a benzyloxycarbonyl radical which, after hydrogenolysis in the presence of palladium on charcoal, yields 2,6-diaminopimelamic acid.

The reaction of a copper salt, such as cupric bromide or basic copper carbonate, with 2,6-diaminopimelamic acid produces a complex which may be represented by the formula:

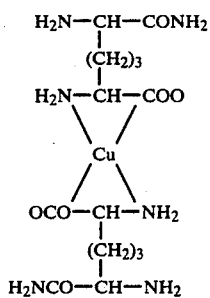

whose free amine functions are protected by reaction with a benzyl haloformate. The complex thus formed is displaced by reaction with hydrogen sulphide to give the product of formula (I).

N⁶-Benzyloxycarbonyl-2,6-diaminopimelamic acid is obtained from 2,6-dibenzyloxycarbonylaminopimelamic acid in an overall yield close to 9%.

It has now been found, and it is this that forms the subject of the present invention, that N⁶-benzyloxycarbonyl-2,6-diaminopimelamic acid of formula (I) may be obtained from 2,6-dibenzyloxycarbonylaminopimelic acid in a markedly improved yield by means of a process comprising fewer stages.

According to the present invention, N⁶-benzyloxycarbonyl-2,6-diaminopimelamic acid is obtained by reaction of an amidation agent with O¹-p-nitrobenzyl-N²-benzyloxycarbonyl-2,6-diaminopimelic acid. The amidation is generally carried out at a temperature in the region of 20° C. with an aqueous ammoniacal solution, in the presence of a water-immiscible solvent chosen from aromatic hydrocarbons (e.g. toluene), halogenated aliphatic hydrocarbons (e.g. methylene chloride), ethers (e.g. ethyl ether) or esters (e.g. ethyl acetate).

O¹-p-Nitrobenzyl-N²-benzyloxycarbonyl-2,6-diaminopimelic acid may be obtained by the reaction of O¹-p-nitrobenzyl-2,6-dibenzyloxycarbonylaminopimelic acid with an agent capable of converting an acid into a corresponding acyl halide, such as phosphorus pentachloride, phosphorus tribromide or thionyl chloride, followed by hydrolysis of the product.

Phosphorus pentachloride is preferably employed, the operation being carried out in an organic solvent such as methylene chloride at a temperature of between 0° and 30° C.

O¹-p-Nitrobenzyl-2,6-dibenzyloxycarbonylaminopimelic acid may be prepared from 2,6-diaminopimelic acid according to the process described by A. Arendt et al., Roczniki Chemii Ann. Soc. Chim. Polonorum, 48, 1501 (1974) [Chem. Abstr., 82, 171409 n (1975)].

The process according to the present invention makes it possible, by starting from an O¹-p-nitrobenzyl-2,6-dibenzyloxycarbonylaminopimelic acid in L,L or D,D or racemic form, to obtain N⁶-benzyloxycarbonyl-2,6-diaminopimelamic acid in L,L or D,D or racemic form, respectively.

Starting from 2,6-dibenzyloxycarbonylaminopimelic acid, N⁶-benzyloxycarbonyl-2,6-diaminopimelamic acid is obtained, according to the process of the present invention, in an overall yield which is generally higher than 20%.

The following Examples show how the invention may be put into practice.

EXAMPLE 1

O¹-p-Nitrobenzyl-N²-benzyloxycarbonyl-L,L-2,6-diaminopimelic acid (57.9 g) is added to a mixture of 20% aqueous ammonia (1.24 l) and ethyl acetate (175 cc). The materials are stirred at approximately 20° C. for 24 hours. The aqueous phase is separated by gravity phase separation and is washed 3 times with ethyl acetate (600 cc in all), and is then cooled to about 10° C. and is lastly neutralized to pH=6 by adding anhydrous acetic acid (250 cc). A slurry is obtained, and is stirred for ½ hour at about 5° C. It is filtered, and the insoluble material is washed twice with acetic acid (400 cc in all) and twice with ethyl acetate (400 cc in all). After evaporation of the solution obtained under reduced pressure (20 mm Hg; 2.7 kPa), N⁶-benzyloxycarbonyl-L,L-2,6-diaminopimelamic acid (23.5 g) is obtained, whose characteristics are as follows:

Rf=0.46 [silica gel; n-butanol-pyridineacetic acid-water (50-20-6-24 by volume)], Rf=0.44 [silica gel; ethyl acetate-acetic acid-water (40-12-10 by volume)], after methylating hydrolysis (boiling 6N hydrochloric in methanol) followed by acylation with trifluoroacetic anhydride, determination by gas phase chromatography on a Chirasil-Val column shows that the product obtained contains 99.8% of L,L form and 0.2% of meso form.

$[\alpha]_D^{20} = +18.2°$ (acetic acid, c=0.3)

$O^1$-p-Nitrobenzyl-$N^2$-benzyloxycarbonyl-L,L-2,6-diaminopimelic acid may be prepared as follows:

Phosphorus pentachloride (112.8 g) is added over 15 minutes, in small portions, to a solution, cooled to 5° C., of L,L-$O^1$-p-nitrobenzyl-2,6-dibenzyloxycarbonylaminopimelic acid (268 g) in methylene chloride (4 l). The reaction mixture is stirred for 50 minutes at 5° C. and then for 15 minutes at 20° C. 2 l of methylene chloride are then removed from the reaction mixture over 50 minutes by distillation at ordinary pressure. Petroleum ether (6.66 l) is added to the concentrate, cooled to 5° C. The mixture is left at 5° C. for 24 hours and the ether phase is then removed. The residual oil is triturated 3 times with petroleum ether (1.5 l in all) and is then dissolved in methylene chloride (1 l). After concentration to dryness under reduced pressure (20 mm Hg; 2.7 kPa) at 50° C., the porous cake obtained is dissolved in anhydrous acetic acid (1.74 l). Water (0.87 l) is added to this solution.

The mixture is left at 20° C. for 24 hours, and the solution is then poured into a mixture of water (7.2 l) and ether (2 l). The aqueous phase is adjusted to pH=5 by slow addition of sodium carbonate (400 g). The precipitate formed is separated off by filtration, and is washed successively twice with distilled water (1 l in all) and 3 times with ether (1.5 l in all). After drying in open air, and then under reduced pressure (20 mm Hg; 2.7 kPa) at 50° C., $O^1$-p-nitrobenzyl-$N^2$-benzyloxycarbonyl-L,L-2,6-diaminopimelic acid (169.3 g), whose characteristics are as follows, is obtained:

Rf=0.61 [silica gel; n-butanol-pyridine-acetic acid-water (50-20-6-24 by volume)].

$O^1$-p-Nitrobenzyl-$N^2$-benzyloxycarbonyl-L,L-2,6-diaminopimelic acid may be prepared according to the method of A. Arendt et al., Roczniki Chemii Ann. Soc. Chim. Polonorum, 48, 1501 (1974).

EXAMPLE 2

$O^1$-p-Nitrobenzyl-$N^2$-benzyloxycarbonyl-D,D-2,6-diaminopimelic acid (10.4 g) is added to a mixture of 20% strength aqueous ammonia (226 cc) and ethyl acetate (35 cc). The mixture is stirred for 3 hours at a temperature in the region of 20° C. The aqueous phase is separated by gravity phase separation, is washed 3 times with ethyl acetate (120 cc in all) and is partially concentrated to pH=7 under reduced pressure (20 mm Hg; 2.7 kPa) at 50° C. This produces a slurry, which is cooled to 4° C., for 1 hour, and is filtered and washed 3 times with water (30 cc in all). After drying under reduced pressure (20 mm Hg; 2.7 kPa) at 20° C., $N^6$-benzyloxycarbonyl-D,D-2,6-diaminopimelamic acid (5.36 g), whose characteristics are as follows, is obtained:

Rf=0.46 [silica gel; n-butanol-pyridine-acetic acid-water (50-20-6-24 by volume)].

$O^1$-p-Nitrobenzyl-$N^2$-benzyloxycarbonyl-D,D-2,6-diaminopimelic acid may be prepared in the same manner as the L,L-isomer.

Thus, by starting from D,D-$O^1$-p-nitrobenzyl-2,6-dibenzyloxycarbonylaminopimelic acid (26.57 g), phosphorus pentachloride (11.18 g) and methylene chloride (460 cc), $O^1$-p-nitrobenzyl-$N^2$-benzyloxycarbonyl-D,D-2,6-diaminopimelic acid (10.44 g), whose characteristics are as follows, is obtained:

Rf=0.61 [silica gel; n-butanol-pyridine-acetic acid-water (50-20-6-24 by volume)].

D,D-$O^1$-p-Nitrobenzyl-2,6-dibenzyloxycarbonylaminopemelic acid may be prepared according to the method of A. Arendt et al., Roczniki Chemii Ann. Soc. Chim. Polonorum, 48, 1501 (1974).

EXAMPLE 3

By following the same procedure as in Example 2, starting from $O^1$-p-nitrobenzyl-$N^2$-benzyloxycarbonyl-DD,LL-2,6-diaminopimelic acid (52.38 g), 20% strength aqueous ammonia (1900 cc) and ethyl acetate (270 cc), $N^6$-benzyloxycarbonyl-DD,LL-2,6-diaminopimelamic acid (26.58 g), whose characteristics are as follows, is obtained:

Rf=0.46 [silica gel; n-butanol-pyridine-acetic acid-water (50-20-6-24 by volume)].

$O^1$-p-Nitrobenzyl-$N^2$-benzyloxycarbonyl-DD,LL-2,6-diaminopimelic acid may be prepared in the same manner as the L,L isomer.

Thus, by starting from DD,LL-$O^1$-p-nitrobenzyl-2,6-dibenzyloxycarbonylaminopimelic acid (114 g), phosphorus pentachloride (48 g) and methylene chloride (1.5 l), $O^1$-p-nitrobenzyl-$N^2$-benzyloxycarbonyl-DD,LL-2,6-diaminopimelic acid (52.9 g), whose characteristics are as follows, is obtained:

Rf=0.61 [silica gel; n-butanol-pyridine-acetic acid-water (50-20-6-24 by volume)].

DD,LL-$O^1$-p-Nitrobenzyl-2,6-dibenzyloxycarbonylaminopimelic acid may be prepared according to the method of A. Arendt et al., Roczniki Chemii Ann. Soc. Chim. Polonorum, 48, 1501 (1974).

We claim:

1. A process for the preparation of $N^6$-benzyloxycarbonyl-2,6-diaminopimelamic acid in L,L or D,D or racemic form, which comprises reacting an amidation agent with $O^1$-p-nitrobenzyl-$N^2$-benzyloxycarbonyl-2,6-diaminopimelic acid in L,L or D,D or racemic form.

2. A process according to claim 1, wherein the substituted diaminopimelic acid used as starting material has been obtained by the reaction of an agent capable of converting an acid into a corresponding acyl halide, chosen from phosphorus pentachloride, phosphorus tribromide and thionyl chloride, with $O^1$-p-nitrobenzyl-2,6-dibenzyloxycarbonylaminopimelic acid in L,L or D,D or racemic form.

3. Process according to claim 1, wherein the amidation is carried out with an aqueous solution of ammonia in a water-immiscible organic solvent chosen from aromatic hydrocarbons, halogenated aliphatic hydrocarbons, ethers and esters.

4. Process according to claim 3, wherein the said solvent is ethyl acetate.

* * * * *